Patent Number: 4,992,577
… Date of Patent: Feb. 12, 1991

[54] PREPARATION OF 3-VINYL-SUBSTITUTED 2,2-DIMETHYLCYCLOPROPANE-1-CARBOXYLIC ACIDS AND ESTERS AND INTERMEDIATES THEREFOR

[75] Inventors: Reinhard Lantzsch, Leverkusen; Dieter Arlt, Cologne; Manfred Jautelat, Burscheid, all of Fed. Rep. of Germany

[73] Assignee: Bayer Aktiengesellschaft, Leverkusen, Fed. Rep. of Germany

[21] Appl. No.: 355,578

[22] Filed: May 22, 1989

Related U.S. Application Data

[63] Continuation of Ser. No. 484,802, Apr. 14, 1983, abandoned.

[30] Foreign Application Priority Data

May 5, 1982 [DE]  Fed. Rep. of Germany ....... 3216790
Aug. 26, 1982 [DE]  Fed. Rep. of Germany ....... 3231814

[51] Int. Cl.$^5$ ............................................. C07C 69/74
[52] U.S. Cl. ...................................... 560/124; 549/78; 549/79; 558/414; 560/8; 560/18; 560/64; 560/65; 560/118; 562/405; 562/432; 562/473; 562/474; 562/500; 562/506; 568/303; 568/308; 568/316; 568/348; 568/376; 568/379; 568/381; 568/393; 568/418; 568/313; 568/345; 568/390
[58] Field of Search ....................... 560/124, 8, 18, 64, 560/65, 118; 562/506, 405, 432, 473, 474, 500; 549/78, 79; 558/414; 568/316, 348, 393

[56] References Cited

U.S. PATENT DOCUMENTS 4,423,243  12/1983  Jautelat ............................... 560/124
4,454,343  6/1984  Kondo ................................. 560/124

FOREIGN PATENT DOCUMENTS 33160  8/1981  European Pat. Off. .
2605398  8/1976  Fed. Rep. of Germany .
2621835  11/1976  Fed. Rep. of Germany .
2742547  3/1978  Fed. Rep. of Germany .
3035149  4/1982  Fed. Rep. of Germany .

OTHER PUBLICATIONS

March "Advanced Organic Chemistry; Reactions, Mechanisms, and Structure," pp. 458–459, (1968).
Adams, "Organic Reactions," vol. 16, pp. 1–4, 9–11, 27–38 & 81 (1968).
Arch. Pharmaz., vol. 308, pp. 422–429.

Primary Examiner—Michael L. Shippen
Attorney, Agent, or Firm—Sprung Horn Kramer & Woods

[57] ABSTRACT

A process for preparing a compound of the formula

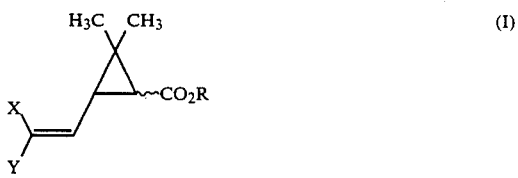

in which
Y is halogen, alkyl or cycloalkyl optionally substituted by halogen or $C_{1-4}$-alkoxy, alkenyl optionally substituted by halogen, aryl, heteroaryl or alkoxycarbonyl,
X is hydrogen, halogen or optionally halogen-substituted alkyl, or
X and Y, together with the adjacent C atom, form a saturated cycloalkphatic ring having up to 6 C atoms, and
R is hydrogen or $C_1$-$C_4$-alkyl, comprising reacting an aldehyde of the formula

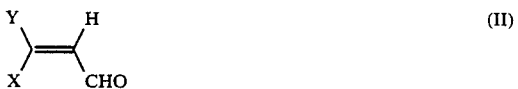

with 2-methylbutan-3-one of the formula

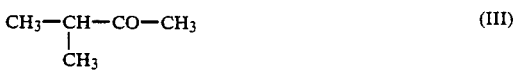

in the presence of a hydrohalic acid thereby to form a 4,4-dimethyl-3-halogeno-1-hexen-5-one of the formula

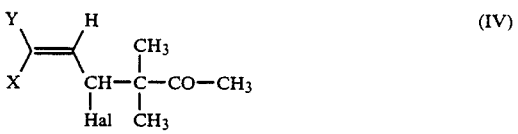

in which
Hal is halogen, halogenating said compound to produce a compound of the formula

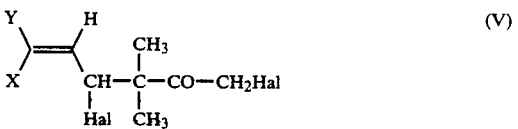

and reacting said compound with a base of the formula

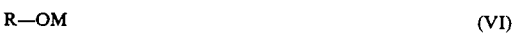

in which
M is one equivalent of an alkali or alkaline earth metal ion.

Compounds IV and V are new. By suitable conditions the trans isomer is selectively produced.

4 Claims, No Drawings

PREPARATION OF 3-VINYL-SUBSTITUTED 2,2-DIMETHYLCYCLOPROPANE-1-CARBOXYLIC ACIDS AND ESTERS AND INTERMEDIATES THEREFOR

This is a continuation of Ser. No. 484,802, filed 4-14-83, now abandoned.

The present invention relates to a new process for preparing 3-vinyl-substituted 2,2-dimethylcyclopropane-1-carboxylic acids and -carboxylates as well as to new intermediate products for these compounds and their preparation.

It has already been disclosed that esters of 3-styryl-2,2-dimethylcyclopropanecarboxylic acids have insecticidal properties (for example German Offenlegungsschriften [German Published Specifications] 2,706,184 and 2,738,150). The compounds are prepared by reacting the corresponding ylides with caronaldehyde in a Wittig reaction (German Offenlegungsschriften [German Published Specifications] 2,738,150 and 2,837,101). These syntheses are expensive, since caronaldehyde is producible only with difficulty. Even by other means, the acids are only accessible via multistage synthetic routes.

It has also been disclosed that esters of 3-dihalogenovinyl-substituted cyclopropanecarboxylic acids have insecticidal properties (DE-OS [German Published Specification] 2,326,077).

The acids are prepared, for example, by reacting 1,1-dihalogeno-4-methylpentadiene with diazoacetates (Farkas et al Coll Czech Comm. Chem. 24, 2,230 (1959)).

They can also be obtained by reacting prenol and orthoacetates to give dimethylpentenoates, adding tetrahalogenomethane and dehydrohalogenating the resulting compounds by means of alcoholates (DE-OS [German Published Specification] 2,539,895).

These processes either require high safety precautions or they are technically involved, since numerous stages have to be passed through. These processes also start from relatively expensive starting products.

1. It has now been found that compounds of the formula (I)

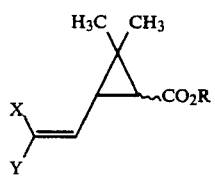

in which
- Y represents halogen, alkyl or cycloalkyl which are optionally substituted by halogen or $C_{1-4}$-alkoxy, alkenyl which is optionally substituted by halogen, substituted or unsubstituted aryl or heteroaryl and alkoxycarbonyl,
- X represents hydrogen, halogen or optionally halogen-substituted alkyl,
- X and Y, together with the adjacent C atom, can represent a saturated cycloaliphatic ring having up to 6 C atoms, and
- R represents hydrogen or $C_1$-$C_4$-alkyl, are obtained by reacting aldehydes of the formula (II)

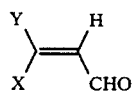

in which
Y and X have the abovementioned meaning, with methylbutan-3-one (III)

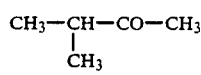

in the presence of hydrohalic acids, halogenating the 4,4-dimethyl-3-halogeno-1-hexen-5-ones which can be obtained in this step and have the formula (IV)

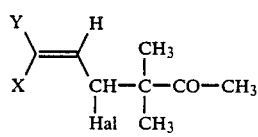

in which
Y and X have the abovementioned meaning and
Hal represents chlorine or bromine, and reacting compounds which can be obtained in this step and have the formula (V)

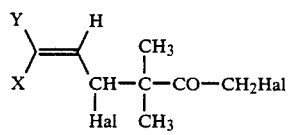

in which
Y, X and Hal have the abovementioned meaning, with bases of the formula (VI)

R—OM                    (VI)

in which
R has the abovementioned meaning and
M represents one equivalent of an alkali or alkaline earth metal ion.

2. New 4,4-dimethyl-3-halogeno-1-hexen-5-ones have also been found, of the formula (IV)

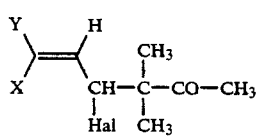

in which
- Y represents halogen, alkyl or cycloalkyl which are optionally substituted by halogen or $C_{1-4}$-alkoxy, alkenyl which is optionally substituted by halogen, substituted or unsubstituted aryl or heteroaryl and alkoxycarbonyl,
- X represents hydrogen, halogen or optionally halogen-substituted alkyl,
- X and Y, together with the adjacent C atom, can represent a saturated cycloaliphatic ring having up to 6 C atoms, and
- Hal represents chlorine or bromine.

3. It has been found that 4,4-dimethyl-3-halogeno-1-hexen-5-ones of the formula (IV)

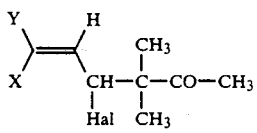
(IV)

in which
Y, X and Hal have the meaning given under 2 hereinabove, are obtained when aldehydes of the formula (II)

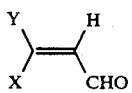
(II)

in which
Y and X have the abovementioned meaning, are reacted with 2-methylbutan-3-one of the formula (III)

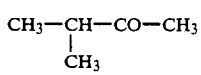
(III)

in the presence of hydrohalic acids.

4. New compounds have also been found, of the formula (V)

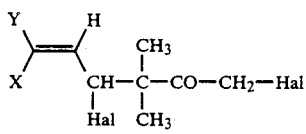
(V)

in which
Y represents halogen, alkyl or cycloalkyl which are optionally substituted by halogen or $C_{1-4}$-alkoxy, alkenyl which is optionally substituted by halogen, substituted or unsubstituted aryl or heteroaryl and alkoxycarbonyl,
X represents hydrogen, halogen or optionally halogen-substituted alkyl,
X and Y, together with the adjacent C atom, can represent a saturated aliphatic ring having up to 6 C atoms, and
Hal independently of each other represent chlorine or bromine.

5. It has also been found that compounds of the formula (V)

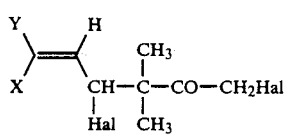
(V)

in which
Y, X and Hal have the meaning given under 4 hereinabove, are obtained when 4,4-dimethyl-3-halogeno-1-hexen-5-ones of the formula (IV)

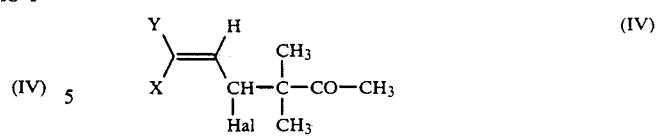
(IV)

in which
Y, X and Hal have the abovementioned meaning, are halogenated.

6. It has also been found that compounds of the formula (I)

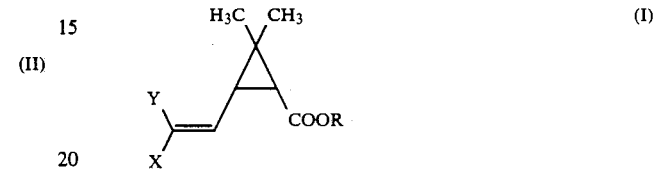
(I)

in which
Y, X and R have the abovementioned meaning, are obtained when compounds of the formula (V)

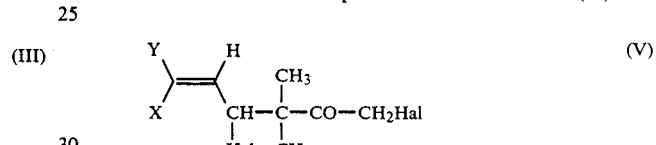
(V)

in which
Y, X and Hal have the abovementioned meaning, are reacted with bases of the formula (VI)

$$R-O-M \quad (VI)$$

in which
R and M have the abovementioned meaning.

4,4-Dimethyl-3-halogeno-1-hexen-5-ones of the formula (IV) (above) are obtained, as already mentioned, by reacting aldehydes of the formula (II)

(II)

with 2-methylbutan-3-one (III) in the presence of hydrogen halides.

The course of the reaction is surprising. According to the state of the art, it was likely that the aldehydes attack at the methyl group of 2-methylbutan-3-one.

Thus, for example, "Crganic Reactions", vol. 16, page 31 at the bottom to page 32 at the top, predicts that it is likely that acid-catalyzed condensations of aldehydes with ketones take place at the methyl group. It is also known that the structure is critical in deciding whether aldehydes react at the $CH_3$ group or at the CH group. Thus, benzaldehyde and 4-chlorobenzaldehyde react with methyl alkyl ketones only in traces at the CH group and predominantly at the $CH_3$ group. On the other hand, 4-methoxybenzaldehyde reacts with methyl alkyl ketones to 70% at the CH group (Archiv fur Pharmazie 308, 422 (1975)).

If, for example, 3-chloro-3-phenylpropenal is used as a starting material, the course of the reaction can be represented by the following equation:

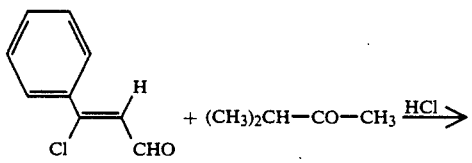

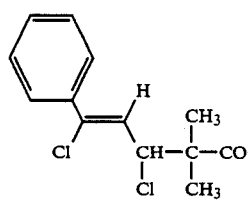

The general formula II gives a definition of starting materials used in this process. In this formula, Y preferably represents halogen, in particular fluorine, chlorine or bromine, $C_{1-4}$-alkyl or cyclopropyl which are optionally substituted by halogen, in particular fluorine or chlorine, dichlorovinyl, optionally halogen-, cyano-, $C_{1-4}$-alkyl-, $C_{1-4}$-halogenoalkyl, $C_{1-4}$-alkoxy, $C_{1-4}$-halogenoalkoxy-, $C_{1-4}$-alkylthio- or $C_{1-4}$-halogenoalkylkthio-substituted phenyl, optionally halogen-substituted thiophene or $C_{1-4}$-alkoxycarbonyl.

X preferably represents hydrogen or halogen, in particular fluorine, chlorine or bromine, or optionally fluorine- or chlorine-substituted $C_{1-4}$-alkyl.

Y particularly preferably represents optionally fluorine-, chlorine-, bromine-, cyano-, methyl-, ethyl-, methoxy-, trigluoromethyl-, trifluoromethoxy- or trifluoromethylmercapto-substituted phenyl, fluorine, chlorine, bromine, methyl or trifluoromethyl.

Y very particularly preferably represents chlorine or chlorine-substituted phenyl.

X preferably represents fluorine, chlorine, bromine or methyl,

X very particularly preferably represents chlorine.

Aldehydes of the formula (II) which are to be used as starting materials are known and can be prepared by known methods (for example Zeitschrift fur Chemie 1976, 16, page 337; Houben Weyl volume 7 (I page 119; and European Patent Specification 31,041). 2-Methylbutan-1-one, a compound also to be used as a starting product, is known.

The reaction is carried out in the presence of at least equimolar amounts of hydrogen chloride or hydrogen bromide.

The reaction can be carried out with or without diluents. Possible diluents are all solvents which are inert to hydrogen chloride or hydrogen bromide, such as, for example, hydrocarbons, such as cyclohexane, petroleum ether, benzene, toluene or chlorohydrocarbons, such as methylene chloride, chloroform, carbon tetrachlorine or chlorobenzene; or ethers, such as diethyl ether, diisopropyl ether, tetrahydrofuran, dioxane or 1,2-dimethoxyethane. Acetic acid can also be used as a solvent.

If the reaction is carried out without a diluent, 2-methyl-3-butanone can be used in excess. Normally, 1–10, preferably 1–4, equivalents of ketone are used per equivalent of aldehyde.

The temperature used is between 0° and 25° C.

The progress of the reaction can be monitored by $^1$H-NMR. The reaction times are between 4 and 24 hours.

The 4,4-dimethyl-3-halogeno-1-hexen-5-ones of the formula (IV) which can be obtained on reacting aldehydes of the formula (II) with the methylbutanone of the formula (III) are new. They can be isolated and purified or they can be immediately reacted further in the next stage without further purification.

Those compounds of the formula (IV) are preferable in which X and Y have the preferable or particularly preferable meaning indicated for compounds of the formula II.

Compounds of the formula (V) are obtained by halogenating compounds of the formula (IV) (above).

The course of this reaction is surprising.

It had to be expected that, in addition to a halogenation of the methyl group, halogen is preferentially added to the double bond. Even a halogenation in the allyl position could not be excluded, in particular since a degree of activation is present due to the halogen atom already present.

It is therefore extremely surprising that the halogenation takes place extremely selectively, under the specified conditions virtually exclusively, at the methyl group.

If, for example, 4,4-dimethyl-1,3-dichloro-1-(3,4-dichlorophenyl)-1-hexen-5-one is used as starting materials and bromine is used as a halogenating agent, the course of the reaction can be represented by the following equation:

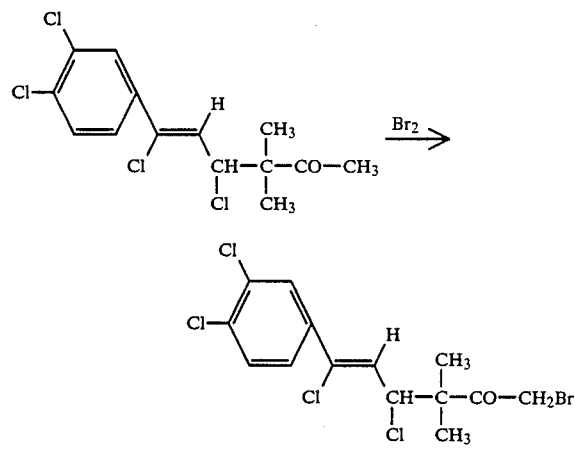

The general formula (IV) gives a definition of starting materials which can be used in the process. In this formula, Y and X have the preferable and particularly preferable meaning indicated hereinabove for compounds of the formula II.

Hal represents chlorine or bromine. Possible halogenating agents are chlorine, bromine or sulphuryl chloride.

The reaction is customarily carried out in an inert diluent. Examples of these are alcohols, such as methanol or ethanol, chlorohydrocarbons, such as methylene chloride, chloroform, carbon tetrachloride, dichloroethane or highly chlorinated aromatics, acids, such as, for example, formic acid or acetic acid, and esters, such as acetates.

The reaction may be carried out in the presence of a catalyst, such as, for example, hydrohalic acids (halogen chloride or hydrogen bromide), or Lewis acids (aluminum chloride, zinc chloride or aluminum bromide).

The reaction temperature should not exceed about +40° C., and the reaction is preferably carried out between −10° and +25° C.

At the most up to one equivalent of halogenating agent was added; but it is possible to use less than the stoichiometric amount in order to prevent a second halogen atom from reacting.

Compounds of the formula (V) which can be obtained on halogenating compounds of the formula (IV) are new. They can be isolated and purified, or they can be immediately reacted further in the next stage without further purification. Those compounds of the formula (V) are preferable and particularly preferable in which the substituents Y and X have the preferable meanings indicated for compounds of the formula (IV).

Compounds of the formula (I) (above) are obtained when compounds of the formula (V) are reacted with bases of the formula (VI).

The reaction is surprising since it is known that similar compounds, such as, for example,

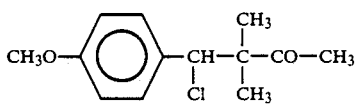

react even under extremely mild conditions with aqueous bases or alcohols and carbonates to give alcohols or ethers (Archiv der Pharmazie 308, 422 and 313, 795):

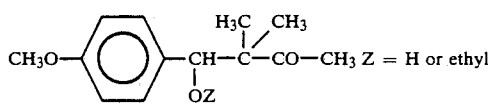

The advantage of the reaction according to the invention is that it starts from inexpensive readily available starting products. It therefore enables cyclopropane carboxylates of the formula I to be preferred in a particularly economical manner.

A further advantage is that this reaction enables a stereoselective synthesis of compounds which are asymetrically substituted at the vinyl double bond.

If, for example, 4,4-dimethyl-1,3-dichloro-6-bromo-1-(4-fluorophenyl)-1-hexen-5-one is used as a starting material and sodium hydroxide is used as the base, the course of the reaction can be represented by the following equation:

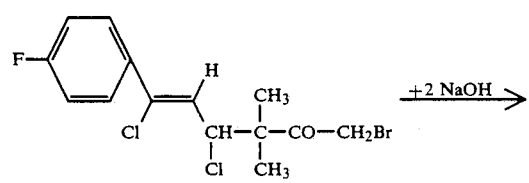

-continued

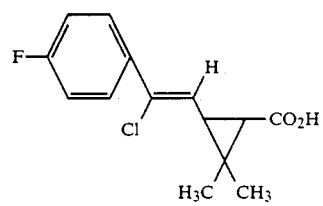

The general formulae (V) and (VI) give a definition of starting materials which can be used in the process. In these formulae, Y, X and Hal have the abovementioned preferable and particularly preferable meaning.

Specific examples which may be mentioned of bases are sodium hydroxide, potassium hydroxide, calcium hydroxide, sodium methylate, sodium ethylate, sodium butylate and potassium tert.-butylate.

If the hydroxides are used, the reaction is preferably carried out in water and/or an inert diluent. Possible examples of the latter are alcohols, such as methanol, ethanol or tert.-butanol, ethers, such as dioxane, tetrahydrofuran, dimethoxyethane, ketones, such as acetone, or dimethylformamide. However, it is also possible to use solvents which are not miscible with water, such as methylene chloride, petroleum ether, cyclohexane, toluene or chlorobenzene, if appropriate in the presence of a phase transfer catalyst.

If the alcoholates are used, the reaction is most advantageously carried out in the corresponding alcohols.

At least 2 equivalents of base (VI) must be used per one mol of starting material of the formula (V). An excess of base up to 10 equivalents is usually advantageous.

The reaction temperatures can be varied within a relatively wide range, but the reaction can surprisingly be accomplished even under extremely mild conditions. The reaction is generally carried out between 0° C. and 150° C., but it is preferably carried out between 20° and 100° C.

The reaction mixture is worked up if acids are being prepared (R=H) by extraction in an alkaline medium (to remove impurities) and, after acidification of the water phase, by renewed extraction. In the preparation of esters, purification is effected by distillation. Beforehand the mixture is diluted with water, neutralized and extracted.

Under the indicated conditions cis/trans mixtures of the acids are produced approximately in a ratio of 25:75 to 35:65. However it was surprisingly found that under certain conditions the trans-acids are almost exclusively obtained. Thus it is for example possible to prepare very pure trans3-[Z-2'-chloro-2'-(p-Cl-phenyl)-vinyl]-2,2-dimethyl -cyclopropane carboxylic acid which according to the hitherto existing prior art was only able to be prepared by chlorination and renewed dechlorination with metals from a transE/Z-acid mixture (cf. DE-OS 30 35 149).

In order to obtain the purest possible trans acids potassium hydroxide or sodium hydroxide are preferably used as bases; they may also contain water; the use of pulverized technical grade potassium hydroxide is particularly preferred. The solvents used are alcohols, such as methanol, ethanol, propanol and glycol monomethyl ether. Methanol is particularly preferred.

The cis-content decreases as the temperature increases. If too high a temperature is selected the yield decreases, for example by the elimination of hydrogen chloride and the formation of a triple bond. Thus the optimum temperature for each acid has to be found. This is between about 20° C. and 150° C., preferably however between about 40° and 100° C.

EXAMPLE 1

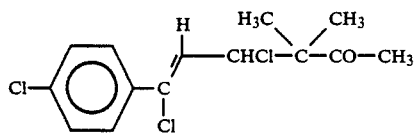

Hydrogen chloride is passed at 10° C. until saturation into a mixture of 20.1 g (0.1 mol) of 3-chloro-3-(4-chlorophenyl)-propenal and 34.4 g (0.4 mol) of methyl isopropyl ketone. The mixture is allowed to stand overnight and then poured onto water, and the resulting mixture is neutralized by means of sodium carbonate. The neutralized mixture is extracted with methylene chloride and dried, and methylene chloride and excess methyl isopropyl ketone are distilled off. 24.9 g remain of crude 4,4-dimethyl-1,3-dichloro-1-(4-chlorophenyl)-1-hexen-5-one, which is purified by means of distillation in a high vacuum. 22.2 g (72.7% of theory) are obtained of a colorless or sightly yellowish oil having a boiling point of 150°-155° C./0.1 mbar and a melting point of 42°-43° C.

EXAMPLE 2

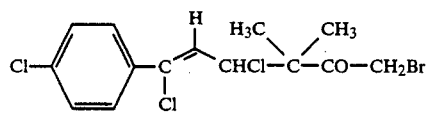

10 g (0.0325 mol) of 4,4-dimethyl-1,3-dichloro-1-(4-chlorophenyl)-1-hexen-5-one are dissolved in 200 ml of chloroform, and 5.2 g of bromine (0.0325 mol) are added dropwise at 20° C. The mixture is stirred for 1 hour at room temperature, and the solvent is distilled off. 12.5 g are obtained of an oil which very largely consists of 4,4-dimethyl-1,3-dichloro-6-bromo-1-(4-chlorophenyl)-1-hexen-5-one.

$^1$H-NMR (CDCl$_3$)=$\delta$=1.5 ppm (6H,m); 4.2 ppm (2H,s); 5.23 ppm (1H, d, J=5Hz); 6.19 ppm (1H, d, J=5 Hz); 7.2–7.6 ppm (4H,m).

EXAMPLE 3

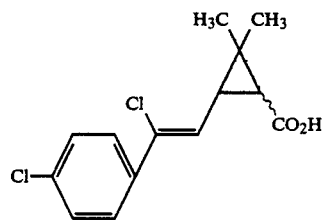

12 g (0.031 mol) of 4,4-dimethyl-1,3-dichloro-6-bromo-1-(4-chlorophenyl)-1-hexen-5-one in 50 ml of dioxane are added dropwise to a solution of 12.45 g (0.31 mol) of sodium hydroxide in 115 ml of water and 100 ml of dioxane at 20° C. The mixture is stirred for 12 hours at room temperature, diluted with 750 ml of water, and extracted with methylene chloride. The water phase is acidified by means of hydrochloric acid and also extracted with methylene chloride. The acidic extracts are dried and the methylene chloride is distilled off. The final solvent residues (dioxane) are removed by drying in a high vacuum at 60° C. The product which remains consists of cis/trans-3-(Z-2-chloro-2-(4-chlorophenyl)-vinyl)-2,2-dimethylcyclopropane-carboxylic acid and has a melting point of 128°–135° C.

EXAMPLE 4

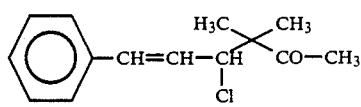

20 g (0.15 mol) of cinnamaldehyde and 25.8 g (0.3 mol) of methyl isopropyl ketone are initially introduced, and dry hydrogen chloride is passed in at 10° C. until saturation. The mixture is stirred for 12 hours at 20°–25° C. and poured onto water, and the resulting mixture is neutralized by means of sodium carbonate. The neutralized mixture is extracted with methylene chloride and dried, and the methylene chloride is distilled off. 25.7 g (72.4% of theory) are obtained of 1-phenyl-3-chloro-4,4-dimethyl-1-hexen-5-one which has a melting point of 71° C.

EXAMPLE 5

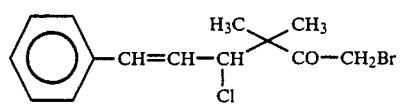

5 g (0.021 mol) of 1-phenyl-3-chloro-4,4-dimethyl-1-hexen-5-one are dissolved in 40 ml of chloroform, and 3.38 g (0.021 mol) of bromine are added dropwise at 20° C. The solvent is distilled off after one hour. 6.8 g remain of an oil which mainly consists of 1-phenyl-3-chloro-6-bromo-4,4-dimethyl-1-hexen-5-one and is directly further reacted.

EXAMPLE 6

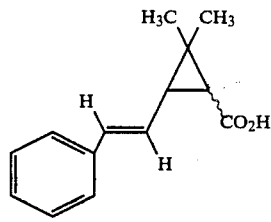

6 g of crude (from Example 5) 1-phenyl-3-chloro-6-bromo-4,4-dimethyl-1-hexen-5-one in 50 ml of dioxane are added dropwise to a solution of 8.8 g of sodium hydroxide in 80 ml of water and 50 ml of dioxane, and the mixture is stirred for 12 hours at 20° C. The mixture is then diluted with water and extracted with methylene chloride. The aqueous phase is acidified by means of hydrochloric acid and also extracted with methylene chloride. The acidic extracts are dried, and the methylene chloride is distilled off. The final solvent residues (dioxane) are removed by drying in a high vacuum at 60° C. The product which remains consists of cis/trans-3-styryl-2,2-dimethylcyclopropane-carboxylic acid. The structure is confirmed by the $^1$H-NMR spectrum.

EXAMPLE 7

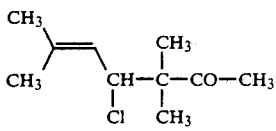

Hydrogen chloride is passed at 10° C. until saturation into a mixture of 42 g (0.5 mol) of 3,3-dimethylacrolein and 86 g (1 mol) of methyl isopropyl ketone, and the mixture is then stirred for 12 hours (without further cooling).

The batch is poured onto ice water, and the resulting mixture is neutralized by means of sodium carbonate. The neutralized mixture is extracted three times with methylene chloride, and the combined organic phases are washed with water and dried with sodium sulphate. After the methylene chloride has been distilled off, 97 g remain of an oil which is distilled in high vacuum. 59 g (62.6% of theory) are obtained of 2,5,5-trimethyl-4-chloro-2-hepten-6-one which has a boiling point of 70°-80° C./0.05 mbar.

EXAMPLE 8

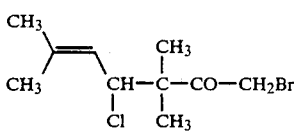

6.03 g (0.032 mol) of 2,5,5-trimethyl-4-chloro-2-hepten-6-one are dissolved in 75 ml of chloroform, 2 drops of an ethereal hydrogen chloride solution are added, and 5.12 g (0.032 mol) of bromine are then added in one portion at 25° C. The mixture is stirred for 2.5 hours at room temperature, and hydrogen bromide and solvent are distilled off in vacuo; the final residues are removed in a high vacuum. 8.7 g are obtained of crude, 2,5,5-trimethyl-4-chloro-7-bromo-2-hepten-6-one, the structure of which is confirmed by the $^1$H-NMR spectrum. It is used directly in the next stage:

EXAMPLE 8a

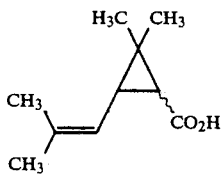

11.96 g (0.299 mol) of sodium hydroxide are dissolved in 107.64 g of water, and 8 g of crude 2,5,5-trimethyl-4-chloro-7-bromo-2-hepten-6-one (from the preceding Example) in 25 ml of dioxane are added dropwise, and the mixture is stirred for 12 hours at room temperature. It is then diluted with water and extracted three times with methylene chloride. The aqueous phase is acidified and also extracted three times with methylene chloride, and the organic phases are dried and concentrated. 3.2 g remain of a crystalline residue which consists of cis-/trans-chrysanthemic acid.

EXAMPLE 9

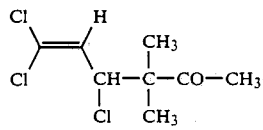

Hydrogen chloride is passed at 10° C. until saturation into a mixture of 19 g (0.08 mol) of dichloroacrolein and 27.52 g (0.32 mol) of methyl isopropyl ketone, and the mixture is then stirred for 12 hours (without further cooling). The batch is poured onto ice water, and the resulting mixture is neutralized by means of sodium carbonate. The neutralized mixture is extracted three times with methylene chloride, and the combined organic phases are washed with water and dried with sodium sulphate. After the solvent has been distilled off, 22 g remain of 1,1,3-trichloro-4,4-dimethyl-1-hexen-5-one, which is distilled off in a high vacuum. Boiling point: 80° C. (0.05 mbar) $^1$H-NMR: δ (CDCl$_3$): 1.2 ppm (S, 6H), 2.2 ppm (S, 3H), 4.95 ppm (d, 1H), 6.05 ppm (d, 1H).

EXAMPLE 10

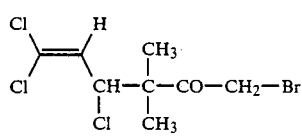

11.475 g (0.05 mol) of 1,1,3-trichloro-4,4-dimethyl-1-hexen-5-one are dissolved in 150 ml of chloroform, and 8 g (0.05 mol) of bromine are added without cooling. The mixture is stirred for 3 hours at room temperature, and hydrogen bromide and solvent are distilled off in vacuo; the final residues are removed in a high vacuum. 15.5 g are obtained of crude 1,1,3-trichloro-6-bromo-4,4-dimethyl-1-hexen-5-one, the structure of which is confirmed by the $^1$H-NMR spectrum. It is used directly in the next stage:

EXAMPLE 10a

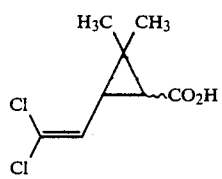

3.6 g (0.09 mol) of sodium hydroxide are dissolved in 36.4 g of water, and 9.255 g (0.03 mol) of crude 1,1,3-trichloro-6-bromo-4,4-dimethyl-1-hexen-5-one are added. The mixture is then heated at 80° C. for 15 minutes, and allowed to cool down. After the mixture has been diluted with water, it is extracted with methylene chloride. The aqueous phase is acidified and again extracted.

Drying and concentrating produce 6.05 g of cis-/trans-permethrinic acid. Yield: 96.5%.

EXAMPLE 11

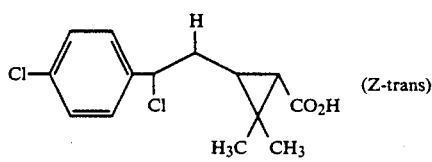 (Z-trans)

52 ml of a 3N methanolic KOH solution (contains 9.93 g=0.156 mols of 88% strength technical grade, pulverized KOH) are initially introduced and 10 g of crude 4,4-dimethyl-1,3-dichloro-6-bromo-1-(4-chlorophenyl)-1-hexen-5-one are passed in at 50° C. After 15 minutes the mixture is cooled and stirred for a further 6 hours. The mixture is then diluted with water (pH-value: 11) and extracted three times with methylene chloride. The aqueous phase is acidified with hydrochloric acid and also extracted three times with methylene chloride. The acidic extracts are dried and the methylene chloride is distilled off. The final solvent residues are removed by drying in a high vacuum at 60° C. The acid which remains (6.1 g) has, according to gas chromatographic analysis (silylated sample) a content of 92.9%. Yield: 90%. By recrystallizing once from cyclohexane pure trans-3-(Z-2-chloro-2-(4-chlorophenyl)-vinyl)-2,2-dimethyl-cyclopropane-1-carboxylic acid is obtained.

EXAMPLE 12

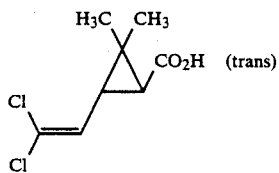 (trans)

200 ml of a 3N methanolic KOH solution (contains 38.2 g=0.6 mols of 88% strength technical grade, pulverized KOH) are initially introduced and 30.85 g (0.1 mol) of 1,1,3-trichloro-6-bromo-4,4-dimethyl-1-hexen-5-one are passed in at 60° C. After 15 minutes the mixture is allowed to cool and is stirred for further 10 hours at room temperature. The mixture is diluted with water (pH-value: 11) and extracted three times with methylene chloride. The aqueous phase is acidified with hydrochloric acid and also extracted three times with methylene chloride. The acidic extracts are dried and the methylene chloride is distilled off. The final solvent residues are removed by drying in a high vacuum at 60° C. The remaining trans-2,2-dichlorovinyl-3,3-dimethyl-cyclopropane-1-carboxylic acid weights 19,65 g (94% yield of theory.

It is understood that the specification and examples are illustrative but not limitative of the present invention and that other embodiments within the spirit and scope of the invention will suggest themselves to those skilled in the art.

We claim:

1. A process for preparing a compound of the formula

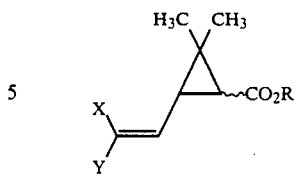

in which

Y is halogen, alkyl or cycloalkyl optionally substituted by halogen or $C_{1-4}$-alkoxy, alkenyl optionally substituted by halogen, aryl, heteroaryl or alkoxycarbonyl, X is hydrogen, halogen or optionally halogen-substituted alkyl, or X and Y, together with the adjacent C atom, form a saturated cycloaliphatic ring having up to 6 C atoms; and R is hydrogen or $C_1$–$C_4$-alkyl, comprising reacting an aldehyde of the formula

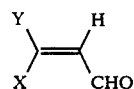

with 2-methylbutan-3-one of the formula

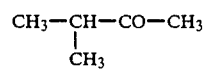

in the presence of a hydrohalic acid thereby to form a 4,4-dimethyl-3-halogeno-1-hexen-5-one of the formula

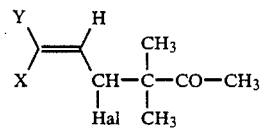

in which

Hal is halogen, halogenating said compound to produce a compound of the formula

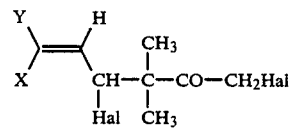

and reacting said compound with a base of the formula

in which

M is one equivalent of an alkali or alkaline earth metal ion.

2. A process according to claim 1, in which

Y is halogen, $C_{1-4}$-alkyl or cyclopropyl optionally substituted by halogen, dichlorovinyl, phenyl, phenyl substituted by halogen, cyano, $C_{1-4}$-alkyl, $C_{1-4}$-halogenalkyl, $C_{1-4}$-alkoxy, $C_{1-4}$-halogenoalkoxy, $C_{1-4}$-alkylthio or $C_{1-4}$-halogenoalkylthio, thiophene, halothiophene or $C_{1-4}$-alkoxycarbonyl, and X is hydrogen, halogen, $C_{1-4}$-alkyl, fluoro-$C_{1-4}$-alkyl or chloro-$C_{1-4}$-alkyl.

3. A process according to claim 1, in which
Y is chlorine or chlorine-substituted phenyl, and
X is fluorine, chlorine, bromine or methyl.

4. A process for preparing a compound of the formula

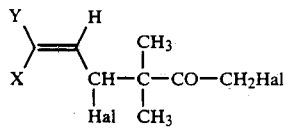

in which
Y is halogen, alkyl or cycloalkyl optionally substituted by halogen or $C_{1-4}$-alkoxy, alkenyl optionally substituted by halogen, aryl, heteroaryl or alkoxycarbonyl,
X is hydrogen, halogen, or optionally halogen-substituted alkyl, or
X and Y, together with the adjacent C atom form a saturated cycloaliphatic ring having up to 6 C atoms, and
Hal each independently is chlorine or bromine, comprising halogenating a 4,4-dimethyl-3-halogeno-1-hexen-5-one of the formula

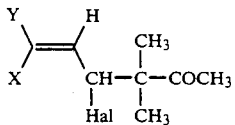

* * * * *